(12) United States Patent
McGuire

(10) Patent No.: US 6,217,599 B1
(45) Date of Patent: Apr. 17, 2001

(54) DEVICE AND METHOD FOR TENDON HARVESTING

(76) Inventor: David A. McGuire, 3418 Lakeside Dr., Anchorage, AK (US) 99515

( * ) Notice: Subject to any disclaimer, the term of this patent is extended or adjusted under 35 U.S.C. 154(b) by 0 days.

(21) Appl. No.: 09/321,373

(22) Filed: May 27, 1999

Related U.S. Application Data

(62) Division of application No. 08/964,501, filed on Nov. 5, 1997, now Pat. No. 5,911,730.
(60) Provisional application No. 60/030,202, filed on Nov. 5, 1996.

(51) Int. Cl.[7] ................................................. A61B 17/32
(52) U.S. Cl. ........................................................ 606/184
(58) Field of Search .................................... 606/184, 183, 606/185, 180, 170

(56) References Cited

U.S. PATENT DOCUMENTS 5,690,662 * 11/1997 Chiu et al. ........................ 606/184
5,827,316 * 10/1998 Young et al. ...................... 606/184
5,910,153 * 6/1999 Mayenberger .................... 606/184

* cited by examiner

Primary Examiner—Michael Buiz
Assistant Examiner—Kevin Truong
(74) Attorney, Agent, or Firm—Bromberg & Sunstein LLP

(57) ABSTRACT

A device for harvesting a tendon for cruciate ligament surgery includes an elongated outer member and an inner member disposed within the outer member, such that the outer and inner members are reciprocally movable relative to one another. The outer member has, at its distal end, a cutting edge for cutting connective tissues about the periphery of the tendon. The inner member is provided with a distal end and pathway into which the tendon is received during the harvesting procedure. The device further includes an actuator for moving the outer member and inner member between a non-actuated position, wherein the distal end of the outer member and the distal end of the inner member are at least in substantially even alignment, and an actuated position, wherein the distal end of the outer member is advanced beyond the distal end of the inner member, so as to expose the cutting edge for separating connective tissues about the periphery of the tendon.

23 Claims, 3 Drawing Sheets

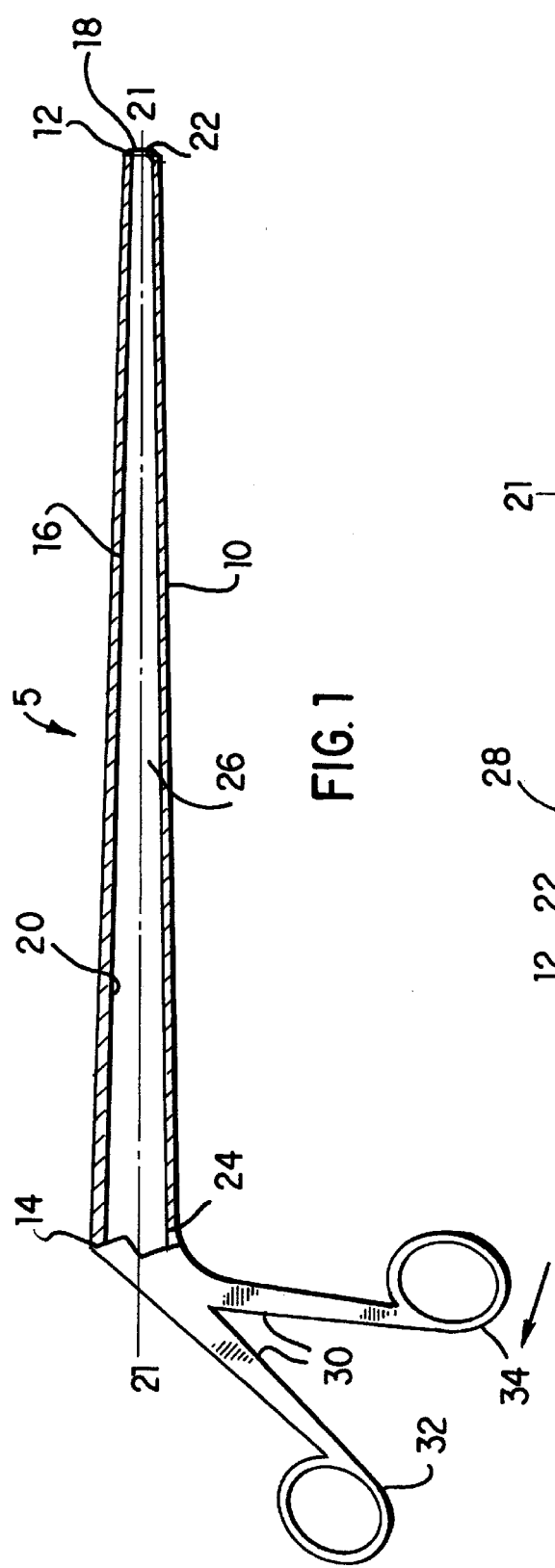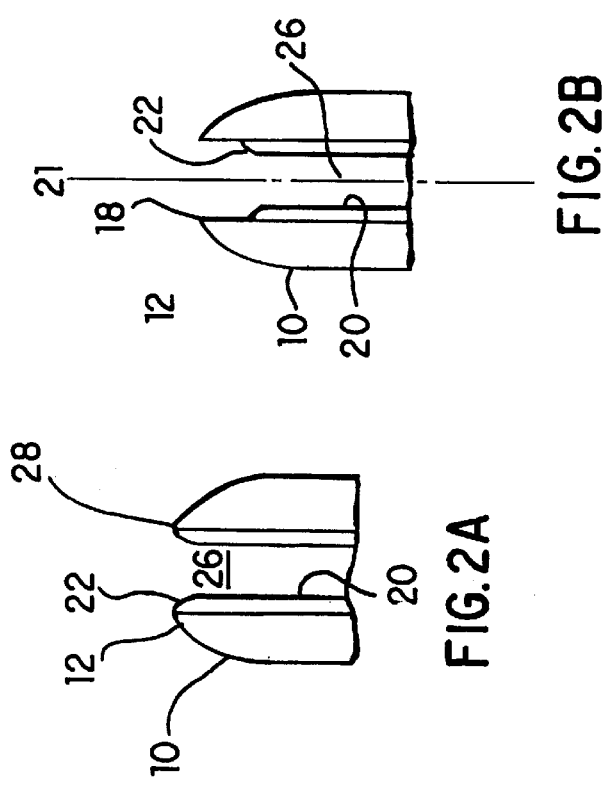

DEVICE AND METHOD FOR TENDON HARVESTING

RELATED U.S. APPLICATIONS

This application is a division of U.S. Application Ser. No. 08/964,501 filed Nov. 5, 1997, now U.S. Pat. No. 5,911,730 which claims priority from Provisional Application Ser. No. 60/030,202, filed Nov. 5, 1996 now pending. These applications are hereby incorporated herein by reference.

TECHNICAL FIELD

The present invention relates to surgical devices, and in particular, devices for harvesting a strip of tendon, for instance, a semitendinosus tendon, for use in cruciate ligament surgery. Methods for tendon harvesting are also set forth.

BACKGROUND ART

When performing cruciate ligament reconstruction, a bone tunnel is formed in the tibia and in the femur so that each end of a ligament replacement graft, for example, a bone-tendon-bone graft, may be inserted into a tunnel and the ligament replacement graft secured between the tibia and the femur. Cruciate ligament reconstruction procedures are described, for example, in U.S. Pat. Nos. Re. 34,871 and 5,562,669, both of which are hereby incorporated herein by reference. A ligament replacement graft may be a patellar tendon, a semitendinosus tendon, or other ligament replacement tissues generally attached to and between a pair of bone blocks, which have been sized for a close fitting engagement within one of the femoral and tibial tunnels. The ligament replacement attached to and between the pair of bone blocks is generally a tendon or a strip of tendon which has been harvested, i.e., stripped of the soft tissues about the periphery of the tendon, and detached from the muscle and the bone, such as the tibia More often than not, however, there is an abundance of soft tissues disposed about the periphery of the tendon, which may make harvesting the tendon a rather slow, difficult and tedious process. In particular, the soft tissues tend to prevent the tendon from being cleanly isolated for detachment from the muscle and bone. Moreover, when attempting to separate the soft tissues from the periphery of the tendon so that a clean strip of tendon may be harvested, there is an increased risk of severing the tendon itself.

Currently, there are several devices adapted for harvesting a tendon or strip of tendon for use in cruciate ligament reconstruction. These tendon harvesting devices are typically designed to separate the soft tissues from the periphery of the tendon by severing the connective tissues between the tendon and the soft tissues. One design provides a patellar tendon harvesting device with a double-bladed scalpel for separating the soft tissues simultaneously along opposite sides of the tendon. However, because the double-bladed scalpel has a cutting surface along the bottom edge of each blade, and separation of the soft tissues from the tendon must be performed by pushing each blade down along each side of the tendon, the sharp blades must be kept substantially parallel to the sides of the tendon to avoid the risk of severing the tendons.

Another design provides a patellar tendon harvesting device with a single cutting blade mounted on a straight handle. The single-bladed device, which has a cutting surface along the bottom edge of the blade, must also be pushed so that the blade moves along the side of the tendon in order to sever the connective tissues between the tendon and the surrounding soft tissues. However, since the instrument is designed with only one blade, a separate cut along each side of the tendon must be performed. In addition, like the double-bladed design, there is nothing between the tendon and the blade of the single-bladed device to protect the integrity of the tendon from being compromised. As a result, when harvesting a tendon or strip of tendon with a single-bladed device, the amount of time, as well as the risk of severing the tendon, may increase.

There are also devices that are designed to harvest a semitendinosus tendon. In general, these devices are cylindrical in shape and are provided with a circular cutting blade at the leading edge. Some may have a slot to permit insertion of the tendon into the circular blade and along the device. Overall, these devices are designed so that the circular cutting blade may be pushed over the tendon to sever the peripheral connective tissues. A few of these devices are designed to rotate as they move over the tendon in order to sever the connective tissues. Of course, if the user is not careful, the sharp circular cutting blade, whether being pushed or rotating, can sever the tendon as it is moved.

To reduce the risk of severing the tendon being harvested, other tendon harvesting devices depend on blunt dissection to sever the connective tissues attaching the soft tissues to the periphery of the tendon. However, because the devices are blunt, the soft tissues may not always be cleanly or efficiently separated from the tendon.

SUMMARY OF THE INVENTION

The present invention, in a preferred embodiment provides, a surgical device that can rapidly, accurately and safely harvest a tendon or strip of tendon, for example, an achilles tendon, a semitendinosus tendon or gracilis, or other autogenic or allogenic tendinosus material. The device is also designed to protect the tendon from being severed during the harvesting process. In accordance with one embodiment of the invention, the device includes an outer member and an inner member disposed within the outer member. The outer member is provided with a distal end for separating soft tissues from the periphery of the tendon, and a passageway extending longitudinally through the outer member. The inner member includes a distal end and a pathway through which one end or a portion of the tendon may be received. The device further includes an actuator disposed so as to cause movement of the outer member longitudinally relative to the inner member between a non-actuated position and an actuated position. In an embodiment of the invention, the actuator includes a pair of handles attached to the inner and outer members, so that when the handles are moved toward one another, the outer member is pushed from the non-actuated position into the actuated position. In the non-actuated position, the distal end of the outer member is at least in substantially even alignment with the distal end of the inner member so as to form a blunt end on the device. In the actuated position, the outer member is urged beyond the inner member, up to a predetermined distance, in order to expose the distal end of the outer member for removing soft tissues from the periphery of the tendon. A cutting edge may also be included circumferentially about the distal end of the outer member to facilitate a clean separation of the soft tissues from the tendon.

A tendon, for example, a semitendinosus tendon, may be harvested in accordance with one embodiment of the present invention by first locating the tendon and directing one end of the tendon, through the distal end, and within the pathway of the inner member, when the inner and the outer members are in the non-actuated position. Next, the actuator is operated, so as to advance the cutting edge at the distal end of the outer member along a portion of the tendon and beyond the distal end of the inner member. In a preferred embodiment, the distal end of the outer member is advanced by a distance of between approximately 2 millimeters (mm) and approximately 5 mm beyond the distal end of the inner member. By advancing the distal end of the outer member along such a distance, the cutting edge may be made to move in a short, accurate, and controlled manner to sever connective tissues present between the tendon and the soft tissues. It should be appreciated that advancement of the cutting edge in such a short and controlled manner along the length of the tendon helps to maintain the integrity of the tendon by protecting the tendon from being accidentally severed. Once the cutting edge has severed the connective tissues between the tendon and the surrounding soft tissues to expose a stripped portion on the tendon, the outer member is retracted so as to pull the cutting edge to a position in even alignment with the distal end of the inner member. In this nonactuated position wherein the distal ends of the outer and inner members are to be at least in substantially even alignment, the device is provided with a blunt end proximal to the newly exposed portion on the tendon. By making the end of the device blunt, the tendon is protected from movements which may otherwise cause the cutting edge to sever the tendon. The entire device is then pushed forward so as to simultaneously move the outer member and inner member along the length of the tendon, while directing the recently stripped portion of the tendon to within the cannulated inner member. While within the cannulated inner member, the stripped portion of the tendon is further protected from being accidentally severed by the cutting edge on the outer member. The outer and inner members may continue to be advanced distally along the tendon until the members again meet resistance from the connective tissues between the tendon and the soft tissues. Examples of the connective tissues between the tendon and the soft tissues may include, but are not limited to, adhesions, and aberrant or normal insertions of collagen tissues into the tendon. In the presence of such resistance, the outer member may again be actuated to expose the cutting edge for severing the connective tissues between the tendon and the surrounding soft tissues. Because the separation of the tendon from the soft tissues is accurate and controlled, the above-described process may be repeated in a rapid manner until a strip of tendon of a desired length is obtained.

BRIEF DESCRIPTION OF THE DRAWINGS

FIG. 1 is a cross-sectional side view of a tendon harvesting device in accordance with one embodiment of the present invention.

FIG. 2A is a partial cross-sectional side view of the device of FIG. 1 at its distal end showing the device in a non-actuated position.

FIG. 2B is a partial cross-sectional side view of the device of FIG. 1 at its distal end showing the device in an actuated position.

DETAILED DESCRIPTION OF THE PREFERRED EMBODIMENTS

Figure 3A:
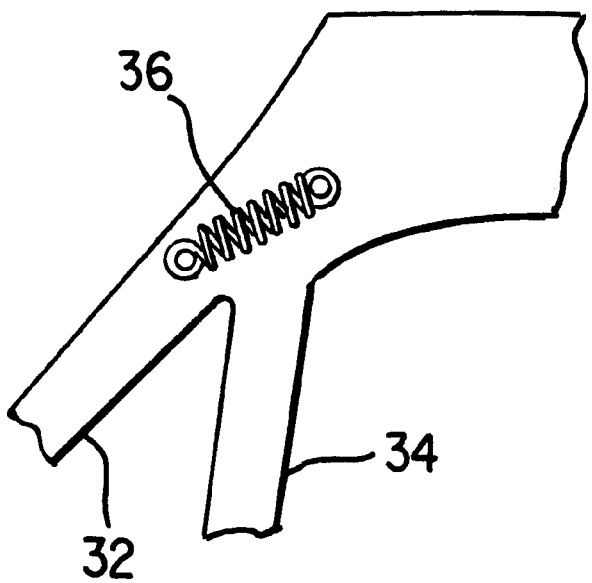
FIG. 3A is a side view of a spring in a naturally contracted position between two handles attached to the device shown in FIG. 1.

Referring now to the drawings, FIG. 1 illustrates a device 5 for harvesting a tendon. In accordance with a presently preferred embodiment, the device 5 comprises an elongated outer member 10, an elongated inner member 20 disposed within the outer member 10, and actuator 30 to reciprocally move the outer member 10 and the inner member 20 relative to one another.

The outer member 10, as shown in FIG. 1, is generally cylindrical in shape and includes a distal end 12, a proximal end 14, and a passageway 16 extending longitudinally between the distal end 12 and the proximal end 14. To facilitate removal of soft tissues from the periphery of a tendon, a cutting edge 18, which is generally sharp, is provided circumferentially about the distal end 12, such that the cutting edge 18 conforms substantially to the cross-sectional shape of the passageway 16 of the outer member 10.

The inner member 20, also substantially cylindrical in shape, is designed to slidably fit within the passageway 16 of the outer member 10. The inner member 20, defining a longitudinal axis 21, includes a distal end 22, a proximal end 24, and a central pathway 26 extending from the distal end 22 to the proximal end 24 of the inner member 20. When the inner member 20 is situated within the outer member 10, the inner member 20 and the outer member 10 are capable of reciprocally moving relative to one another between a non-actuated position and an actuated position. Because the device 5 is designed so that the inner member 20 and outer member 10 may reciprocally slide relative to one another, the inner and outer members may be provided with any desired cross-sectionally shapes that would permit reciprocal movement, for example, elliptical, ovoid, even square.

Looking now at FIG. 2A, when the outer member 10 and inner member 20 are in the non-actuated position, the distal end 12 of the outer member 10 is at least in approximate alignment with the distal end 22 of the inner member 20 to form a blunt end 28. By providing the device 5 with a blunt end 28, the sharp cutting edge 18 of the outer member 10 may be prevented from unnecessarily damaging a tendon when the device 5 is maneuvered in a manner which may otherwise damage a tendon. It should be noted that the outer member 10 need not be flush with the distal end 22 of the inner member 20 to provide a blunt end 28. The blunt end 28 may still be formed when the distal end 22 of the inner member 20 extends beyond the cutting edge 18 of the outer member 10 for up to a couple of millimeters. When the outer member 10 and the inner member 20 are moved into an actuated position, as illustrated in FIG. 2B, the outer member 10 is advanced beyond the inner member 20, so as to expose the cutting edge 18 at the distal end 12. The exposed cutting edge 18 on the outer member 10 may be used to sever the connective tissues attaching the tendon and the soft tissues, so that the soft tissues may subsequently be removed from the periphery of the tendon. In one embodiment of the invention, to facilitate a clean separation and removal of the soft tissues from the periphery of the tendon, the distal end 12 of the outer member 10 is designed to taper in toward the longitudinal axis 21. The taper design allows the outer member 10 to push the distal end 12 underneath the soft tissues, so that the cutting edge 18 may cleanly cut the connective tissues at an area immediately close to the periphery of the tendon. The distal end 12 of the outer member 10 need not be tapered as shown in FIGS. 2A and 2B. However, the taper design facilitates operation of the cutting edge 18 for cutting the connective tissues at an area immediately close to the tendon. If such connective tissue is not cut, the harvested tendon may have residual connective tissue fibers hanging from its periphery. The connective tissues between the tendon and the soft tissues may be, for example, adhesions, aberrant or normal insertion of collagen tissue into the tendon.

To facilitate the advancement of the tendon portion that has been stripped of connective tissues into the pathway 26 of the inner member 20, the distal end 22 is designed to taper outwardly away from the longitudinal axis 21 and toward the outer member 10. The tapered design of the distal end 22 allows the tendon to smoothly slide into the pathway 26 when the outer and inner members of the device 5 are advanced distally. In one embodiment of the invention, the tapering on each of the distal ends of the outer and inner members is such that when the respective distal ends are positioned at least substantially evenly aligned with one another, the device 5 is capable of simultaneously moving the outer member 10 and the inner member 20 along and over the periphery of the tendon in a relatively rapid manner, while maintaining a sufficiently dull blunt end 28 to prevent damage to the tendon. As shown in FIGS. 2A and 2B, the tapering of the outer member 10 at its distal end may be more gradual than the tapering of the inner member 20, so that the outer member 10 provides the requisite sharpness when the device is in the actuated position and the inner member 20 provides a dulling effect when the device is in the non-actuated position.

The device 5 further includes an actuator 30 for reciprocally moving the outer member 10 and the inner member 20 longitudinally relative to one another. One example of such an actuator is shown in FIG. 1 as handles 32 and 34. In accordance with an embodiment of the present invention, handle 32 may be fixedly attached to the proximal end 24 of the inner member 20. Handle 34, on the other hand, may be pivotally attached to the proximal end 14 of the outer member 10. In this manner, when a force is applied to the handle 34 in a direction away from the distal end 12 and toward the handle 32 (as shown by the arrow), the handle 34 acts to push the outer member 10 into an actuated position, wherein the outer member 10 moves beyond the distal end 22 of the inner member 20 to expose the cutting edge 18 on the outer member 10. Other suitable arrangements, known in the art, for moving the outer and inner members relative to one another may be used. For example, there may be pair of handles on the outer and inner members, in a manner similar to handles used with a syringe.

Figure 3B:
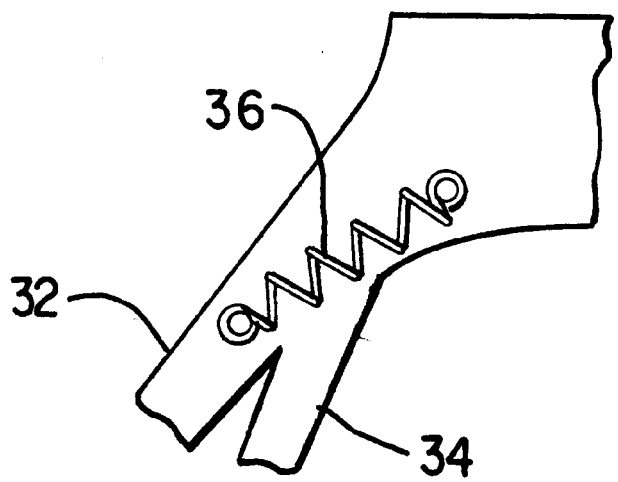
FIG. 3B is a side view of the spring in FIG. 3A in an extended position.

A spring 36, as shown in FIGS. 3A and 3B, may also be provided between the handles 32 and 34, in a region close to the proximal ends of the members, to ensure that the outer member 10 will not move beyond a certain distance past the distal end 22 of the inner member 20. In particular, when the outer member 10 and the inner member 20 are in the non-actuated position, i.e., the distal ends are substantially evenly aligned with one another, the spring 36 is in its naturally contracted position, as shown in FIG. 3A. As a force is applied to move the handle 34 in a direction toward the handle 32, the spring 36 becomes extended, as shown in FIG. 3B, to provide resistance to the force applied, and to limit the distance the handle 34 may move when urging the outer member 10 beyond the distal end 22 of the inner member 20. In one embodiment of the invention, the spring 36 is provided with a resistance which permits the distal end 12 of the outer member 10 to move up to a maximum distance of between about 2 millimeters (mm) and about 5 mm beyond the distal end 22 of the inner member 20. A distance of about 3 mm is presently preferred. Alternatively, or in addition, a suitable mechanical stop may be provided in a manner known in the art to limit the distance which the outer member 10 may move. When the force applied to handle 34 is discontinued, the spring 36 contracts to its natural position to quickly return the outer and inner members from the actuated position to the non-actuated position. To this end, the handles 32 and 34 may be operated in a rapid manner to move the outer and inner members between a non-actuated position and an actuated position. Other mechanisms in lieu of a coil spring having an elastic and/or a shape memory property, and which are capable of providing resistance to the movement of the handle 34, may be used, as for example, an elastic band.

Figure 4A:
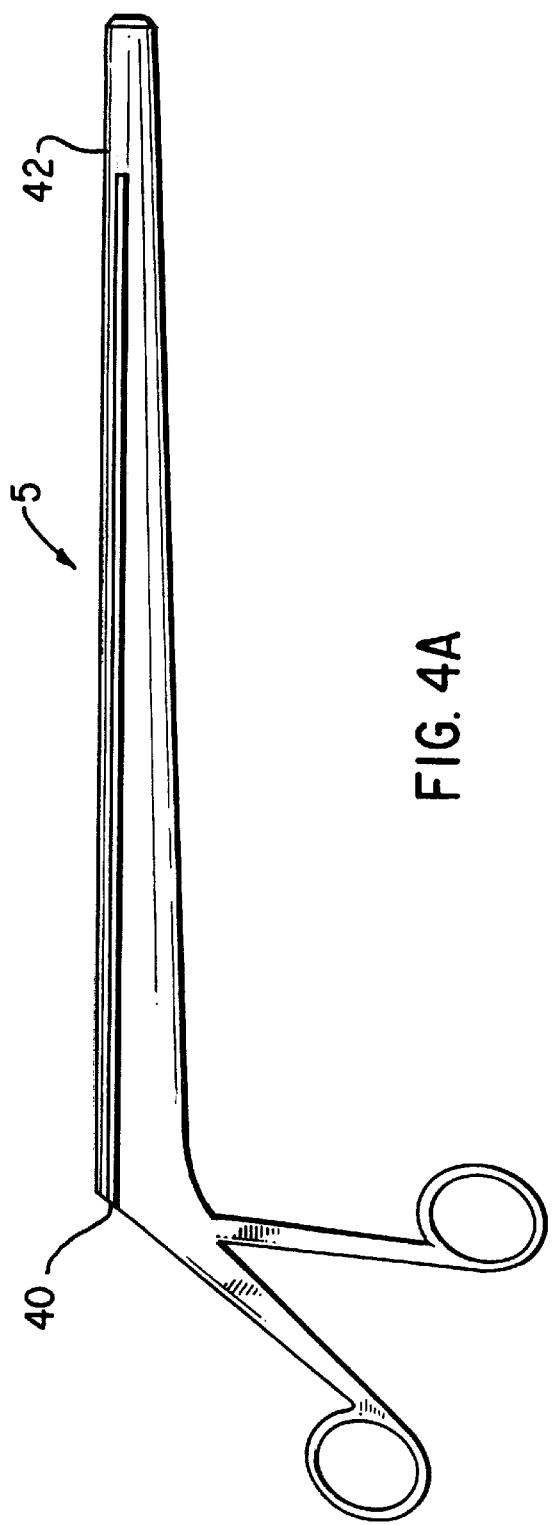
FIG. 4A is a perspective view of the device shown in FIG. 1.
Figure 4B:
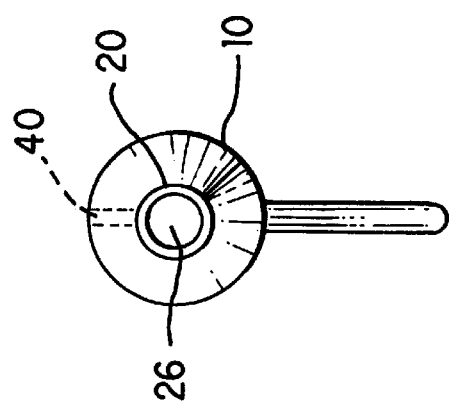
FIG. 4B is a front end view of the device of FIG. 4A.

Turning now to FIGS. 4A and 4B, the device 5, in a further embodiment of the invention, may include a pair of longitudinally disposed slots 40 that are in approximate alignment with one another in each of the inner and outer members. The pair of slots 40, with reference now to FIG. 4B, is designed so that they are in communication with the pathway 26 of the inner member 20. The presence of slots 40 provides an area through which the tendon, once stripped clean of the surrounding soft tissues, may be removed from within the pathway 26 of the inner member 20. The presence of slots 40 also allows the cross section of the outer member 10 to be slightly, so that the outer member 10 may be removed and replaced, if, for instance, the cutting edge 18 on the outer member 10 becomes dull. In a preferred embodiment, member 10 is designed so that only a portion of it, and in particular the cutting edge portion of the member 10, is removable from the device, so that when the cutting edge 18 becomes dull, only the removable portion needs to be replaced. As seen in FIG. 4A, in a preferred embodiment of the invention, slot 40 on the outer member 10 does not extend completely along the length of the outer member 10. Rather, the slot begins at a distance in from the distal end 12 of the outer member 10 to provide the outer member 10 with a solid portion 42. The solid portion 42 facilitates secured movable engagement by the outer member 10 with the distal end 22 of the inner member 20. The outer member 10 or its cutting edge portion may thus be removable or may thus be part of the device 5.

In operation, the device 5 may be used to rapidly, accurately and safely harvest an entire tendon or a portion thereof. To begin harvesting, for example, a semitendinosus tendon for use as a ligament replacement in cruciate ligament surgery, one end of the tendon must first be maneuvered through the distal end 22 and into the pathway 26 of the inner member 20. Next, the outer member 10 may be urged from a non-actuated position (FIG. 2A) into an actuated position (FIG. 2B) to expose the cutting edge 18 on the outer member 10. To urge the outer member 10 into the actuated position, in one embodiment of the invention, a force is applied to the handle 34 to move it in a direction toward the handle 32. By forcing the handle 34 to move in such a manner, as the outer member 10 moves beyond the distal end 22 of the inner member 20, the cutting edge 18 acts to sever any connective tissues immediately present in its path. In a preferred embodiment, the distance along which the distal end 12 of the outer member 10 may move beyond the distal end 22 of the inner member 20 is limited to approximately 3 mm by the spring 36. The shortness of the distance permits the cutting edge 18 to strip the soft tissues from the periphery of the tendon in an accurate and controlled manner, so that the integrity of the tendon may be maintained. In other words, the controlled manner of the stripping process prevents the tendon from being accidentally severed.

Once the portion of tendon immediately proximate to the cutting edge 18 has been stripped of soft tissues, the force applied to the handle 34 may be discontinued, so that the spring 36 may act to retract the outer member 10 into even alignment with the distal end 22 of the inner member 20. The entire device 5 may, thereafter, be advanced distally to simultaneously move the outer and inner members along the tendon, while directing the recently stripped portion of the tendon to within the pathway 26 of the inner member 20. It should be appreciated that the stripped portion of the tendon housed within the pathway 26 is further protected from being accidentally severed by the cutting edge 18 of outer member 10. The outer and inner members may continue to be advanced along the tendon until the blunt end 28, formed by the evenly aligned distal ends of the members, encounters resistance from the distally situated connective tissues between the tendon and the soft tissues. A force may again be applied to the handle 34 so that the outer member 10 may advance beyond the distal end 22 of the inner member 20 to expose the cutting edge 18. By repeatedly alternating the outer and inner members between a non-actuated position and an actuated position, the device 5 may be used to safely and accurately harvest an entire tendon or a portion thereof, in a rapid manner, while minimizing the chances in which the tendon may be severed.

While the invention has been described in connection with specific embodiments thereof, it will be understood that is capable of further modification. For example, any number of various handle designs may be used. Moreover, the angle and shape of the distal ends of the members may also be varied.

What is claimed is:

1. A device for harvesting a tendon comprising:
   an outer member having a distal end and a passageway extending longitudinally through the outer member;
   an inner member disposed within the outer member, the inner member having a distal end and a pathway for receiving the tendon therethrough;
   an actuator disposed so as to cause movement of the outer member longitudinally relative to the inner member between a non-actuated position, wherein the distal end of the inner member is advanced to be at least in substantially even alignment with the distal end of the outer member, and an actuated position, wherein the distal end of the outer member is advanced beyond the distal end of the inner member so as to expose the distal end of the outer member for separating tissues about the periphery of the tendon.

2. A device as set forth in claim 1, wherein the outer member includes a sharp cutting edge circumferentially situated about the distal end of the outer member.

3. A device as set forth in claim 2, wherein the cutting edge is situated on a distal end portion that is removably securable to the outer member.

4. A device as set forth in claim 2, wherein the distal ends of the inner and outer members are shaped so that, in the non-actuated position of the inner and outer members, a blunt end is formed at the distal ends of such members to prevent the sharp cutting edge of the outer member from damaging the tendon.

5. A device as set forth in claim 1, wherein the actuator for causing movement of the outer member relative to the inner member includes a handle.

6. A device as set forth in claim 1, wherein the actuator includes a pair of handles attached to the inner and outer members, so that when the handles are moved toward one another, the outer member is pushed into the actuated position beyond the distal end of the inner member.

7. A device as set forth in claim 1, further comprising an arrangement for biasing the inner and outer members into the non-actuated position from the actuated position.

8. A device as set forth in claim 7, wherein the arrangement includes a spring, the spring capable of defining a distance to which the distal end of the outer member may extend beyond the distal end of the inner member in the actuated position.

9. A device as set forth in claim 8, wherein in the actuated position, the distal end of the outer member extends beyond the distal end of the inner member by a distance of between approximately 2 millimeters (mm) and approximately 5 mm.

10. A device as set forth in claim 9, wherein the distance from which the distal end of the outer member extends beyond the distal end of the inner member is approximately 3 mm.

11. A device as set forth in claim 1, wherein the outer member is removably detachable from the device.

12. A device as set forth in claim 1, wherein the inner and outer members are substantially cylindrical in shape.

13. A device as set forth in claim 1 further including a pair of longitudinally disposed slots in approximate alignment with one another in each of the inner and outer members.

14. A device for harvesting a tendon comprising:
   an elongated outer member having a proximal end, a distal end, and a passageway extending between the proximal end and the distal end;
   a cutting edge situated at the distal end of the outer member, about the passageway, for separating tissues disposed about the periphery of the tendon; and
   an elongated inner member having a proximal end, a distal end, and a pathway positioned between the proximal and distal ends for receiving the tendon therein, the inner member being disposed within the passageway of the outer member for reciprocal movement relative to the outer member between a first position, wherein the distal ends of the outer and inner members are advanced to be at least in substantially even alignment, and a second position, wherein the distal end of the outer member is advanced beyond the distal end of the inner member so as to expose the cutting edge on the outer member for separating tissues about the periphery of the tendon.

15. A device as set forth in claim 14, wherein the distal ends of the inner and outer members are shaped so that, in the non-actuated position of the inner and outer members, a blunt end is formed at the distal ends of such members to prevent the sharp cutting edge of the outer member from damaging the tendon.

16. A device as set forth in claim 14 further including a pair of handles for reciprocally moving the outer member relative to the inner member between the first position and the second position.

17. A device as set forth in claim 16, wherein one of the handles is pivotally mounted to the outer member for reciprocally moving the outer member relative to the inner member between the first position and the second position.

18. A device as set forth in claim 17, wherein, in the second position, the distal end of the outer member extends beyond the distal end of the inner member by a distance of between about 2 mm and about 5 mm.

19. A device as set forth in claim 14, wherein the distal end of the outer ember tapers in toward the passageway of the outer member.

20. A device as set forth in claim 19, wherein the distal end of the inner ember flares out away from the pathway of the inner member.

21. A device as set forth in claim 14 further including a pair of slots longitudinally disposed in approximate alignment with one another in each of the inner and outer members.

22. A device as set forth in claim 14, wherein the outer member is removably detachable from the device.

23. A device as set forth in claim 14, wherein a the distal end on which the cutting edge is situated is removably securable to the outer member.

\* \* \* \* \*